US008995735B2

(12) United States Patent
Cao et al.

(10) Patent No.: US 8,995,735 B2
(45) Date of Patent: Mar. 31, 2015

(54) SYSTEM AND METHOD FOR WIDE CONE HELICAL IMAGE RECONSTRUCTION USING BLENDING OF TWO RECONSTRUCTIONS

(75) Inventors: Guangzhi Cao, Madison, WI (US);
Jiang Hsieh, Brookfield, WI (US);
Brian Edward Nett, Madison, WI (US)

(73) Assignee: General Electric Company, Schenectady, NY (US)

( * ) Notice: Subject to any disclaimer, the term of this patent is extended or adjusted under 35 U.S.C. 154(b) by 366 days.

(21) Appl. No.: 13/478,335

(22) Filed: May 23, 2012

(65) Prior Publication Data

US 2013/0315453 A1 Nov. 28, 2013

(51) Int. Cl.
*G06K 9/00* (2006.01)
*A61B 6/03* (2006.01)
*A61B 6/00* (2006.01)
*G01N 23/04* (2006.01)
*G06T 11/00* (2006.01)

(52) U.S. Cl.
CPC .............. *G06T 11/006* (2013.01); *A61B 6/032* (2013.01); *A61B 6/4085* (2013.01); *G01N 23/046* (2013.01); *G01N 2223/419* (2013.01); *G01N 2223/612* (2013.01); *G01N 2223/643* (2013.01); *G06T 2211/416* (2013.01)
USPC ........................................................ 382/131

(58) Field of Classification Search
None
See application file for complete search history.

(56) References Cited

U.S. PATENT DOCUMENTS

| 5,740,224 | A  | * | 4/1998  | Muller et al. ................... 378/11  |
| 8,023,767 | B1 | * | 9/2011  | Ning et al. ..................... 382/275 |
| 8,270,559 | B2 | * | 9/2012  | Chiang et al. .................... 378/4  |
| 2010/0021033 | A1 | * | 1/2010 | Bruder et al. ................. 382/131 |
| 2013/0077847 | A1 | * | 3/2013 | Hansis et al. ................. 382/131 |
| 2013/0279646 | A1 | * | 10/2013 | Koike et al. .................... 378/15 |
| 2013/0315453 | A1 | * | 11/2013 | Cao et al. ..................... 382/128 |

OTHER PUBLICATIONS

Feldkamp et al., "Practical Cone-Beam Algorithm", J. Opt. Soc. Am. A, vol. 1, No. 6, Jun. 1984, pp. 612-619.
Katsevich, "Theoretically Exact Filtered Backprojection-Type Inversion Algorithm for Spiral CT", Society for Industrial and Applied Mathematics, vol. 62, No. 6, 2002, pp. 2012-2026.
Pack et al., "Cone-Beam Reconstruction Using the Backprojection of Locally Filtered Projections", IEEE Transactions on Medical Imaging, vol. 24, No. 1, Jan. 2005, pp. 70-85.
(Continued)

*Primary Examiner* — Tahmina Ansari
(74) *Attorney, Agent, or Firm* — Ziolkowski Patent Solutions Group, SC (57) ABSTRACT

A tomographic system includes a gantry having an opening for receiving an object to be scanned, a radiation source, a detector positioned to receive radiation from the source that passes through the object, and a computer programmed to acquire a plurality of helical projection datasets of the object, reconstruct a first image using the acquired plurality of helical projection datasets and using a first reconstruction algorithm, reconstruct a second image using the acquired plurality of helical projection datasets and using a second reconstruction algorithm that is different from the first reconstruction algorithm, extract frequency components from each of the first and second images, sum the frequency components from each of the first and second images, and inverse transform the sum of the frequency components to generate a final image.

20 Claims, 5 Drawing Sheets

(56) References Cited

OTHER PUBLICATIONS

Parker, "Optimal Short Scan Convolution Reconstruction for Fanbeam CT", Med. Phys., vol. 9, No. 2, Mar./Apr. 1982, pp. 254-257.

Tang et al., "A Three-Dimensional-Weighted Cone Beam Filtered Backprojection (CB-FBP) Algorithm for Image Reconstruction in Volumetric CT-Helical Scanning", Physics in Medicine and Biology, vol. 51, 2006, pp. 855-874.

Thibault et al., "A Three-Dimensional Statistical Approach to Improved Image Quality for Multislice Helical CT", Med. Phys., vol. 34, No. 11, Nov. 2007, pp. 4526-4544.

Zou et al., "Exact Image Reconstruction on PI-Lines from Minimum Data in Helical Cone-Beam CT", Physics in Medicine and Biology, vol. 49, 2004, pp. 941-959.

Zhuang et al., "Fan-Beam and Cone-Beam Image Reconstruction Via Filtering the Backprojection Image of Differentiated Projection Data", Physics in Medicine and Biology, vol. 49, 2004, pp. 5489-5503.

* cited by examiner

SYSTEM AND METHOD FOR WIDE CONE HELICAL IMAGE RECONSTRUCTION USING BLENDING OF TWO RECONSTRUCTIONS

BACKGROUND OF THE INVENTION

Embodiments of the invention relate generally to tomographic imaging and, more particularly, to an apparatus and method for wide cone helical reconstruction.

Typically, in x-ray systems, such as computed tomography (CT) imaging systems, an x-ray source emits a fan-shaped or cone-shaped beam toward a subject, such as a patient, a piece of luggage, or any other object of interest. Hereinafter, the terms "subject" and "object" shall include anything capable of being imaged. The beam, after being attenuated by the subject, impinges upon an array of radiation detectors. The intensity of the attenuated beam of radiation received at the detector array is typically dependent upon the attenuation of the x-ray beam by the subject. Each detector element of the detector array produces an electrical signal indicative of the attenuated beam received by the detector element. The electrical signals are converted to digital signals and transmitted to a data processing system for analysis, which ultimately produces an image.

Generally, the x-ray source and the detector array are rotated about the gantry within an imaging plane and around the subject. X-ray sources typically include x-ray tubes, which emit the x-ray beam from a focal point. X-ray detectors typically include a collimator for collimating x-ray beams directed toward the detector, a scintillator adjacent to the collimator for converting x-rays to light energy, and photodiodes for receiving the light energy from the scintillator and producing electrical signals therefrom. Typically, each scintillator of a scintillator array converts x-rays to light energy and discharges the light energy to a photodiode adjacent thereto. Each photodiode detects the light energy and generates a corresponding electrical signal. The outputs of the photodiodes are digitized and then transmitted to the data processing system for image reconstruction.

The helical scan is a popular scan mode in clinical computed tomography (CT) diagnostic imaging due to its fast volumetric coverage capability. Traditionally, known algorithms such as Feldkamp-Davis-Kress algorithms (FDK-type algorithms) have been widely used because of the simplicity of the FDK-type algorithms and the desirable image characteristics they produce. However, as the detector size in the Z-direction (or slice direction) in CT applications has increased in recent years, helical reconstruction has become more challenging for FDK-type and other known algorithms due to the increased cone angle in the X-ray beam. Traditional view weighting methods are insufficient to address the increased cone beam artifacts while maintaining the desired noise statistics.

Recently, theoretically exact algorithms have been proposed for helical reconstruction. These types of algorithms can generate a reconstruction image (we use the term image to represent both a 2D image which is a single slice image and a 3D image which is an image volume, hereafter) with little or no cone beam artifacts, however, they also lead to higher noise level due to the difficulty in handling redundant data. More recently, iterative reconstruction (IR) algorithms have also been proposed for CT reconstruction that show great promise in reducing both noise and cone-beam artifacts. However, IR algorithms generally are associated with a significant computational penalty and therefore the reconstruction is much slower than other methods.

Therefore, a new reconstruction approach is desirable for wide cone helical scans having low cone beam artifacts while maintaining simplicity and low noise level.

BRIEF DESCRIPTION OF THE INVENTION

Embodiments of the invention are directed to a method and apparatus for acquiring wide cone imaging data and reconstructing an image having low cone beam artifacts.

According to one aspect of the invention, a tomographic system includes a gantry having an opening for receiving an object to be scanned, a radiation source, a detector positioned to receive radiation from the source that passes through the object, and a computer programmed to acquire a plurality of helical projection datasets of the object, reconstruct a first image using the acquired plurality of helical projection datasets and using a first reconstruction algorithm, reconstruct a second image using the acquired plurality of helical projection datasets and using a second reconstruction algorithm that is different from the first reconstruction algorithm, extract frequency components from each of the first and second images, sum the frequency components from each of the first and second images, and inverse transform the sum of the frequency components to generate a final image.

According to another aspect of the invention, a method of generating an image includes reconstructing first and second images from a set of helical projection datasets using reconstruction algorithms that are different from one another, extracting frequency information from each of the first and second images, summing the extracted frequency data from each of the first and second images, and transforming the summed frequency data using an inverse transform to generate an image.

According to yet another aspect of the invention, a computer readable storage medium having stored thereon a computer program comprising instructions, which, when executed by a computer, cause the computer to obtain helical projection datasets of a subject, reconstruct a first image of the subject using the helical projection datasets and a first reconstruction algorithm and a second image of the subject using the helical projection datasets and a second reconstruction algorithm that is different from the first reconstruction algorithm, extract frequency components from each of the first and second images, blend the extracted frequency components from each of the first and second images to form a blended dataset, and apply an inverse transform to the blended dataset to form an image.

These and other advantages and features will be more readily understood from the following detailed description of embodiments of the invention that is provided in connection with the accompanying drawings.

DETAILED DESCRIPTION

The following description presents a technique for reconstructing wide cone helical images using extracted frequency data from intermediate images formed using different reconstruction techniques.

The operating environment of the invention is described with respect to a sixty-four-slice or beyond computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
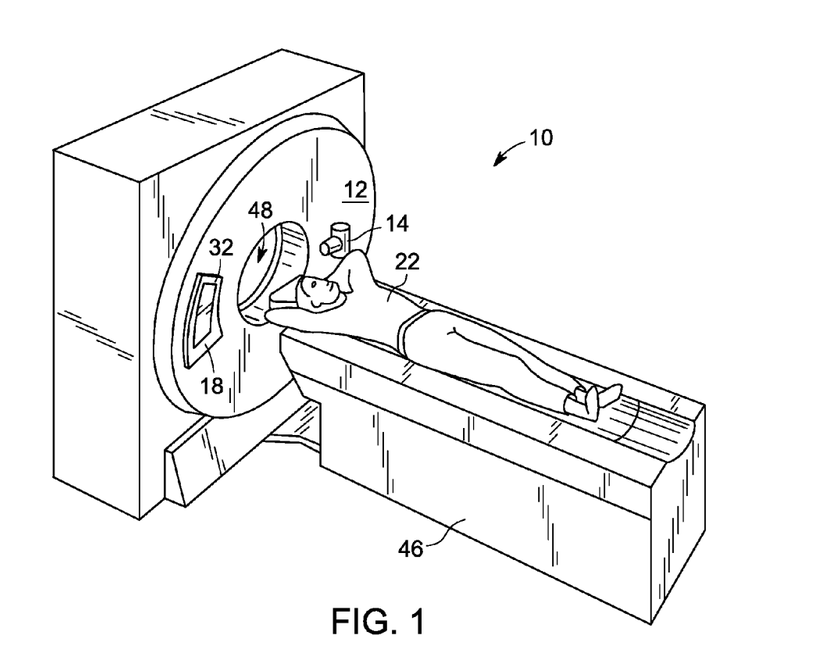
FIG. 1 is a pictorial view of a CT imaging system incorporating embodiments of the invention.
Figure 2:
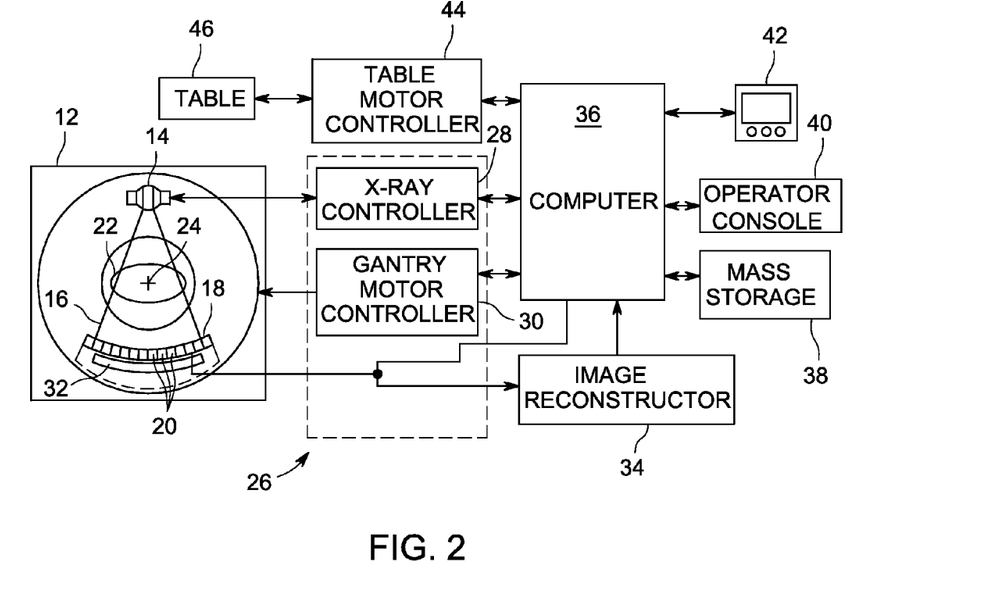
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays 16 that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22.

During a scan to acquire x-ray projection data, gantry 12 and the components mounted thereon rotate about a center of rotation 24. In embodiments, a detector wide enough (i.e., axially along a slice or Z direction of system 10, as is commonly understood in the art) to cover the whole heart or organ of interest in one rotation may be employed to acquire projection data from one or more heart cycles for performing a single segment or a multi-segment reconstruction—hence the desire for increased detector width, or wide cone detectors, which can lead to cone beam artifacts. Typically, "wide cone" refers to a detector width along a Z or slice direction that exceeds 4 cm at isocenter. However, the invention is not to be so limited and is applicable to any detector width, greater or less than 4 cm at isocenter, in which conebeam artifacts may result from imaging data acquired due to the extremes of the detector along the slice direction. Further, in order to image a whole heart, for instance, it may be desirable to have a detector that is 16 cm or greater along the slice direction at isocenter, which can cause yet greater conebeam artifacts due to the extreme length.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. Additionally, the computer 36 may also operate a conveyor system or a table motor controller 44 that, in turn, controls a conveyor system or a motorized table 46 in order to appropriately position the object 22, such as the patient, in the gantry 12.

As such, data may be acquired in an axial or 'step-and-shoot' mode, a helical mode, as one or more segments of a circular scan, or a shuttle mode, as examples, according to the invention. In a step-and-shoot mode, for example, the table 46 may be held stationary during the acquisition of at least part of the projection data. In case of a helical scan, however, the table 46 may be moved in order to move portions of the object 22 through a gantry opening 48 while projection data is being collected and the gantry 12 is rotating to provide a desired "helical pitch." Helical scans are commonly employed because they advantageously eliminate an inter-scan delay that is experienced in a step-and-shoot mode. The helical pitch, as used herein, is a measure of the amount of movement of table 46 per rotation of the gantry 12. According to the invention the helical pitch may be constant during an acquisition or the pitch may be variable, depending on the type of acquisition. In case of a shuttle mode, the object being scanned is moved back and forth while data is acquired in order to obtain, for instance, perfusion data.

Generally, a rate of rotation of the gantry 12 may be adjusted based on the method of data acquisition. In a single segment reconstruction for example, the rate of rotation of the gantry 12 may be based on an acquired electrocardiogram signal corresponding to the patient, and may typically be set to a maximum possible value corresponding to the scanner. In a multi-segment reconstruction, however, the rate of rotation of the gantry 12 may be based on a desired cardiac cycle of the patient or a measured average cardiac cycle rate. Particularly, the DAS 32 may collect projection data from two or more heart cycles such that the combined collected data corresponds to at least 180 degrees plus fan angle for the desired cardiac phase.

Figure 3:
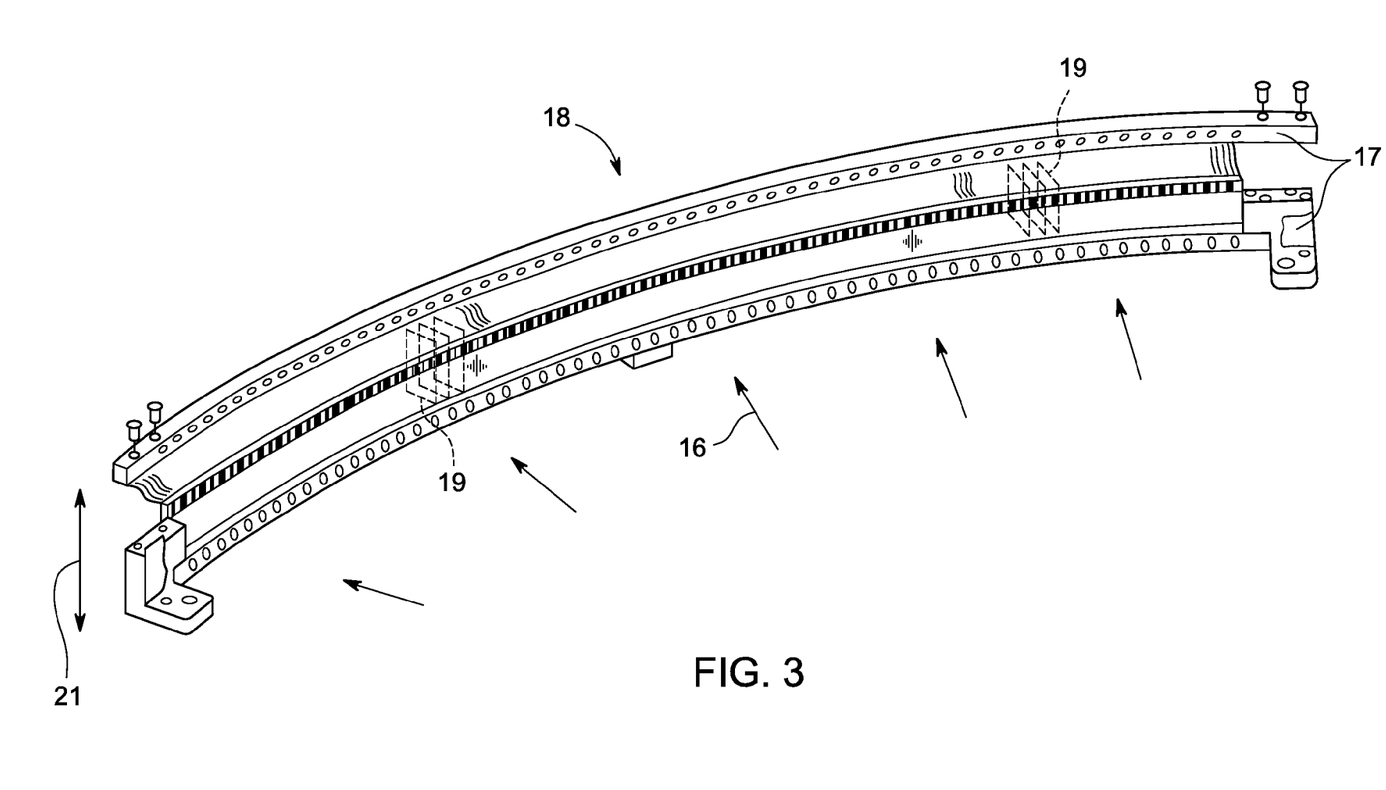
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12 along a slice or Z direction 21.

Figure 4:
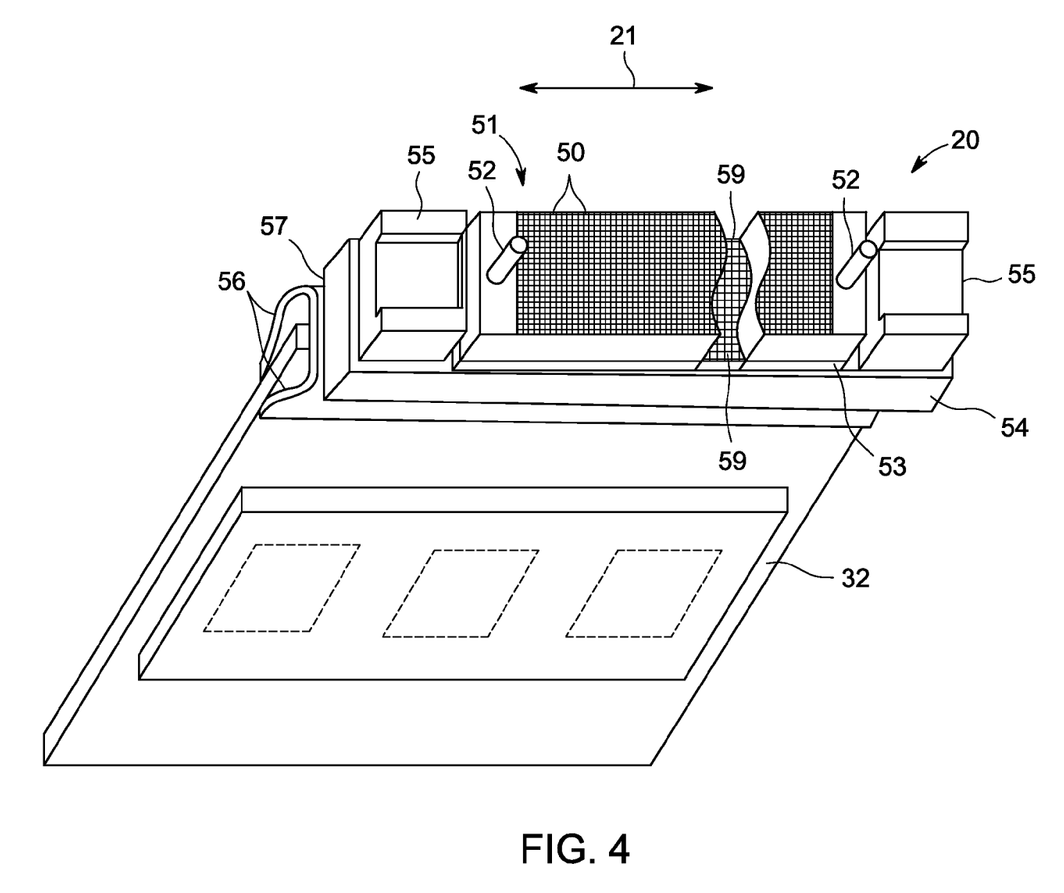
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal. Z direction 21 illustrates the slice direction which, in one embodiment, is 4 cm or greater as measured at isocenter, which corresponds generally to center of rotation 24 as illustrated in FIG. 2.

Further, although exemplary embodiments of the present technique are described in the context of a CT system, it will be appreciated that use of the present technique for improving the images in various other imaging applications and systems is also contemplated. Some of these systems include dual source, two detector CT systems, multi-source CT systems, multi-detector systems, X-Ray systems, positron emission tomography (PET) scanners, single photon emission computed tomography (SPECT) scanners, microscopes, digital cameras, charge coupled devices, or combinations thereof.

Embodiments illustrated hereinafter disclose an imaging system, a computed tomography (CT) system, and methods for reconstructing wide cone helical images. Thus, according to the invention, a reconstruction framework is provided for wide cone helical scans, which is capable of taking advantage of different reconstruction methods. Specifically, the disclosed algorithm first generates two different reconstructions each of which solves or takes into account different challenges in widecone helical reconstruction. By appropriately blending the frequency information of these two reconstructions, the result is a final image that mitigates cone beam artifacts while maintaining the desirable noise and resolution properties.

There are at least two major causes of cone beam artifacts in helical reconstruction: 1) z-truncation, which is due to the fact that some voxels may be outside the x-ray beam for some views, and 2) mishandled frequencies, which are due to the fact that some (redundant) measurements in Radon space (which also may be viewed as frequency measurement) are made more than once for a voxel during a helical scan. The final reconstructed image appropriately takes these redundant measurements into account. In the process of ensuring proper weight of redundant measurements, measurements that are used as discarding measured Radon (frequency) data are associated with a dose penalty. Generally, it is difficult to derive a single reconstruction method that is able to simultaneously handle both of the aforementioned root causes of the cone-beam while still utilizing all the redundant data. Thus, according to the invention, it is possible to use two different reconstructions each of which can handle one of the different aspects of wide cone helical reconstruction. Taking into account the different frequency nature of cone beam artifacts and noise, frequency information of two reconstructions can be blended in order to generate a desired final image.

Figure 5:
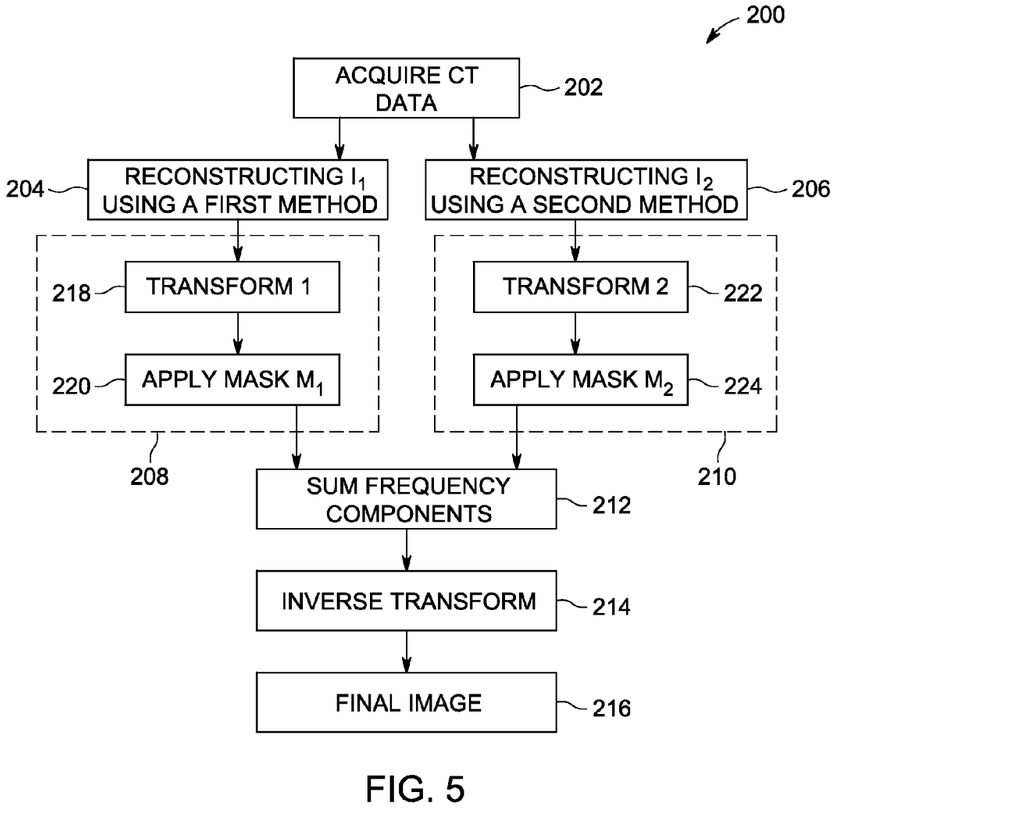
FIG. 5 is a flowchart depicting exemplary steps for reconstructing imaging data, in accordance with aspects of the invention.

Referring now to FIG. 5, technique 200 begins with acquisition of CT data 202 which, as stated may include but is not limited to wide cone helical data. A first reconstruction image $I_1$ is generated using a first method 204 and a second reconstruction image $I_2$ is generated using a second method 206 that is different from the first method. Frequency components are extracted from each of the first and second images, $I_1$ and $I_2$, at respective step 208 and step 210 using a transform and a mask. Each step 208, 210 is configured to extract different frequency components so that, when they are summed or blended at step 212, the frequencies augment each other, as will be described. After summing frequency components at step 212, an inverse of the transform is performed at step 214 and a final image is generated 216.

Various reconstruction methods may be used in order to reconstruct first and second image, $I_1$ and $I_2$, at respective steps 204 and 206, according to the invention. That is, generally the two reconstructions $I_1$ and $I_2$ can be obtained using any two different reconstruction methods that are complementary to each other in terms of the image quality. For example, these two reconstructions can be: both FDK-type reconstructions with different view weighting; FDK-type reconstruction and Katsevich-type exact reconstruction; FDK-type reconstruction and Pi-line type exact inversion; exact analytic method (e.g. Katsevich type or Pi-line type) and iterative reconstruction; or FDK-type reconstruction and iterative reconstruction. More generally, combinations of FDK-type (with different weightings), exact reconstructions (for instance Katsevich type or Pi-line type), and iterative reconstruction may be used to reconstruct first and second image, $I_1$ and $I_2$, at respective steps 204 and 206, so long as the steps are complementary.

Figure 6:
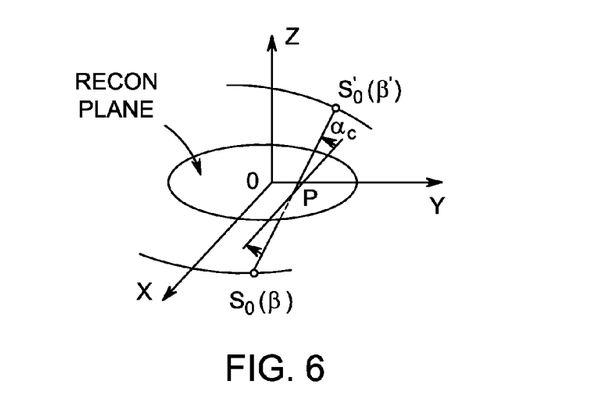
FIG. 6 is a representative of a geometry of a helical reconstruction.

FDK-Type:

a FDK-type algorithm is a well-known cone-beam reconstruction technique. An FDK-type algorithm generally makes use of the full range of data while weighting the projections differently according to the scan geometry, such as in a case of a helical scan with a normalized pitch of 1 for example where the table moves by a detector size during one rotation. In such a case, a $2\pi$ view range is generally used for reconstruction. One known example of 3D view weighting for helical reconstruction in the rebinned cone-parallel geometry is as follows:

$$w_{3D}(\beta, \alpha, \alpha_c) = \frac{w(\beta)\tan^k(\alpha_c)}{w(\beta)\tan^k(\alpha_c) + (1-w(\beta))\tan^k(\alpha)}; \quad \text{Eqn. (1)}$$

where $\beta$ is the view angle, $\alpha$ and $\alpha_c$ are the cone angles of a ray and its conjugate ray, respectively, as illustrated in FIG. 6. Here $w(\beta)$ is a 2D view weighting function which only depends on $\beta$, and k is referred to as the cone-power factor whose value is typically experimentally determined. Thus, a FDK-type algorithm may be applied as at least one of the reconstruction techniques (such as at step 204) which, as stated, may be used in conjunction with another reconstruction technique (at step 206) which may be an exact reconstruction or an iterative reconstruction.

However, as stated, when step 204 is performed with a FDK-type algorithm, step 206 may also be performed also with a FDK-type algorithm of different weighting. Each of the images would likely contain cone beam artifacts since a single view weighting function is not capable of handling both the z-truncation and missing frequencies correctly, while utilizing all the available data. However, a combination of two different view weighting functions will be able to achieve that because each of them can handles one of the root causes, respectively. Specifically, the z-truncation can be easily handled in $I_1$ by reducing the weights of the unmeasured projections. This weight is designed so that all the measured projection data contribute to the final image and the noise properties of the final image. To deal with the mis-handled frequencies due to redundant data, the reconstruction of $I_2$ can be constrained to a minimum projection/data range.

This can be realized either explicitly by short scan view weighting (e.g. Parker weighting), or implicitly by the same 3D view weighting function as in Eqn. (1) with a very large k value. An extreme case is that k=∞, which equivalently leads to $1\pi$ view range for reconstruction for each image voxel. This is an approximation of an exact reconstruction which uses only 1π data for each voxel (e.g. Katsevich type or Pi-line type). In this way, the two images can be obtained from FDK-type reconstructions using different view weighting.

Once the two FDK-type reconstructions, $I_1$ and $I_2$, are obtained, they can be combined together to get the final image. Considering the in-plane low frequency nature of the mis-handled frequencies, the low frequencies of $I_2$ can be blended with the high frequencies of $I_1$, and the resultant final image obtained at step 216 thus possesses the desirable image characteristics of $I_1$ and $I_2$.

Exact-Type (e.g., Katsevich or Pi-Line):

The Katsevich-type and Pi-line type methods are theoretically exact in nature, which means they are capable of achieving mathematically exact reconstruction for helical scans if the scan data satisfy the sufficient condition for exact reconstruction. The exact type reconstruction methods make use of the concept of Pi-line which connects the pixel to be reconstructed and two points on helix. Their implementation is generally filtered backprojection or backprojection filtration which consists of shift-invariant filtering and backprojection. Contrary to the traditional FDK method which applies the ramp filter or modified ramp filter along the detector rows in projection space, the shift-invariant filtering in the exact methods is generally achieved by differentiation of projection followed by the Hilbert transform. The Katsevich-type methods generally apply the Hilbert transform along the tilted lines in the projection space before backprojection, while the Pi-line type methods generally applies the Hilbert transform in the backprojected images of the differentiated projections along the PI-line in image space.

Iterative Reconstruction:

Iterative reconstruction (IR) is a well known technique in which a final image is obtained by iteratively refining intermediate results using a synthesized projection and a measured projection. IR is a reconstruction method that generally formulates the reconstruction as a cost optimization problem and solves the optimization problem to achieve a good reconstruction. The cost function usually consists a term that enforces data matching in projection space and a term that enforces some kind of smoothness in image space. Compared to traditional analytical FDK algorithms and exact-type algorithms whose implementation is generally filtered backprojection or backprojection filtration and the solutions are "closed-form" in nature, IR solves the optimization problem iteratively by iterating between projection and image space.

This known technique begins with an initial guess or estimate of the object's attenuation distribution, and line integrals are calculated of the estimated distribution along the same paths as the original projection measurement. A difference is determined which is used to update the initial guess or estimate in the subsequent iteration, and the process continues until convergence is obtained. As such, according to the invention, one of the steps 204 and 206 can be performed using an iterative reconstruction to generate one of images, $I_1$ and $I_2$.

Thus, first and second images, $I_1$ and $I_2$, at respective steps 204 and 206 may be obtained using complementary reconstruction techniques that include combinations of FDK-type (with different weightings), exact-type (e.g., Katsevich or Pi-line), and iterative reconstruction.

Referring back to steps 208 and 210 of FIG. 5, frequency components are extracted from each of the first and second images, $I_1$ and $I_2$. As shown in FIG. 5, each step 208 and 210 includes a transform step and a mask-application step. That is, step 208 includes a transform step 218 (TRANSFORM 1) and a mask application step 220 (APPLY MASK $M_1$), and step 210 includes a transform step 222 (TRANSFORM 2) and a mask application step 224 (APPLY MASK $M_2$).

Each transform step 218, 222 is conducted using the same type of known transformation algorithms. Such algorithms include but are not limited to a Fast Fourier Transform (FFT) or a wavelet transform, as examples. A FFT, for example and as known in the art, typically includes decomposing a sequence of values into components of different frequencies. Conversely, an inverse FFT may be applied to frequency data to convert back to the sequence of values.

A transform can be viewed as a mathematical function that maps the data from one domain to another domain. Fourier transform (generally implemented as FFT), one of the most common transforms, maps the data (e.g. images) in time/spatial domain to frequency domain. Wavelet transform is another common transform that maps the data in time/spatial domain to the so-called wavelet domain which can be interpreted as a joint time/spatial and frequency domain. Mathematically, the difference between the Fourier transform and the wavelet transform is that they use different basis functions. A key advantage the wavelet transform has over Fourier transform is the temporal/spatial resolution: it captures both frequency and location information after the wavelet transform. Unlike the FFT, there is a family of known wavelet transforms. Among them, the wavelet transforms proposed by I. Daubechies are among the most commonly used in image processing. There are also other transforms such as discrete cosine transform, curvelet transform, Karhunen-Loeve transform, etc. Thus, according to the invention, any known wavelet transform may be applied at steps 218 and 222.

Images $I_1$ and $I_2$ are transformed at respective steps 218 and 222. As stated, the transformations are performed using one of several known methods. However, according to the invention, steps 218 and 222 are each performed having the same type of transformation applied, and an inverse of that same transformation is also applied at step 214. That is, if step 218 includes a FFT, then step 222 likewise includes a FFT and step 214 is an inverse FFT. Or, if step 218 includes a wavelet, then step 222 likewise includes a wavelet and step 214 is an inverse wavelet. In such fashion the image data is transformed (in the FFT example) into the frequency domain. As can be seen, the data used to reconstruct image $I_1$ and $I_2$ derives from the same CT acquisition step 202, but because the two reconstruction techniques 204 and 206 are different from one another, they typically will include different frequency components from one another as well, despite having derived from the same original CT acquisition data.

The masks $M_1$ and $M_2$ determine what type of information can be obtained from reconstructions $I_1$ and $I_2$, respectively determined at steps 204 and 206. Given a transform, it should be a function of the reconstruction methods that are used for reconstructions $I_1$ and $I_2$. In one example reconstructions $I_1$ and $I_2$ are FDK-type reconstructions with different view weighting. High frequency information may be obtained from reconstructions $I_1$ and low frequency information from reconstructions $I_2$. Therefore, if the transform is FFT (assuming a zero frequency is at the center), Mask 2 can be a circular Gaussian mask that keeps the low frequency information, and Mask 1 should be complementary to Mask 2 so that it keeps the high frequency information. If a wavelet transform is used, the logic is the same, i.e., we would still like to combine the high frequency information from reconstructions $I_1$ with low frequency information from reconstructions $I_2$ after the wavelet transform. However, the low frequency region is usually located in the upper-left corner in the wavelet domain. Thus, the shape needs to be adjusted accordingly. In general, therefore, Mask 1 is a high frequency mask, and Mask 2 is a low frequency mask in this case.

As such, mask $M_1$ applied at step 220 and mask $M_2$ applied at step 224 are selected to be complementary to one another. That is, $M_2=1-M_1$. In such fashion, when $M_1$ is applied to transform 1 from step 218, and when $M_2$ is applied to transform 2 from step 222, different frequency components are extracted therefrom. Thus, when the masked frequency components from steps 220 and 224 are blended at step 212 (high frequencies of one image (e.g., $I_1$) and low frequencies of the other image (e.g., $I_2$)), the final image obtained at step 216 thereby possess desirable characteristics of both $I_1$ and $I_2$.

In summary and referring still to FIG. 5, CT image data acquired at step 202 can be reconstructed using two different and known techniques at respective steps 204, 206 to generate images $I_1$ and $I_2$, and frequency components are extracted therefrom at respective blocks 208, 210. The transforms applied at respective steps 218 and 222 are the same type of transform, and a mask ($M_1$) and anti-mask ($M_2$) are respectively applied at steps 220 and 224. Frequency components are blended or summed at step 212 and the inverse transform of the transform applied at steps 218 and 222 is applied at step 214 to form a final image at step 216.

Figure 7:
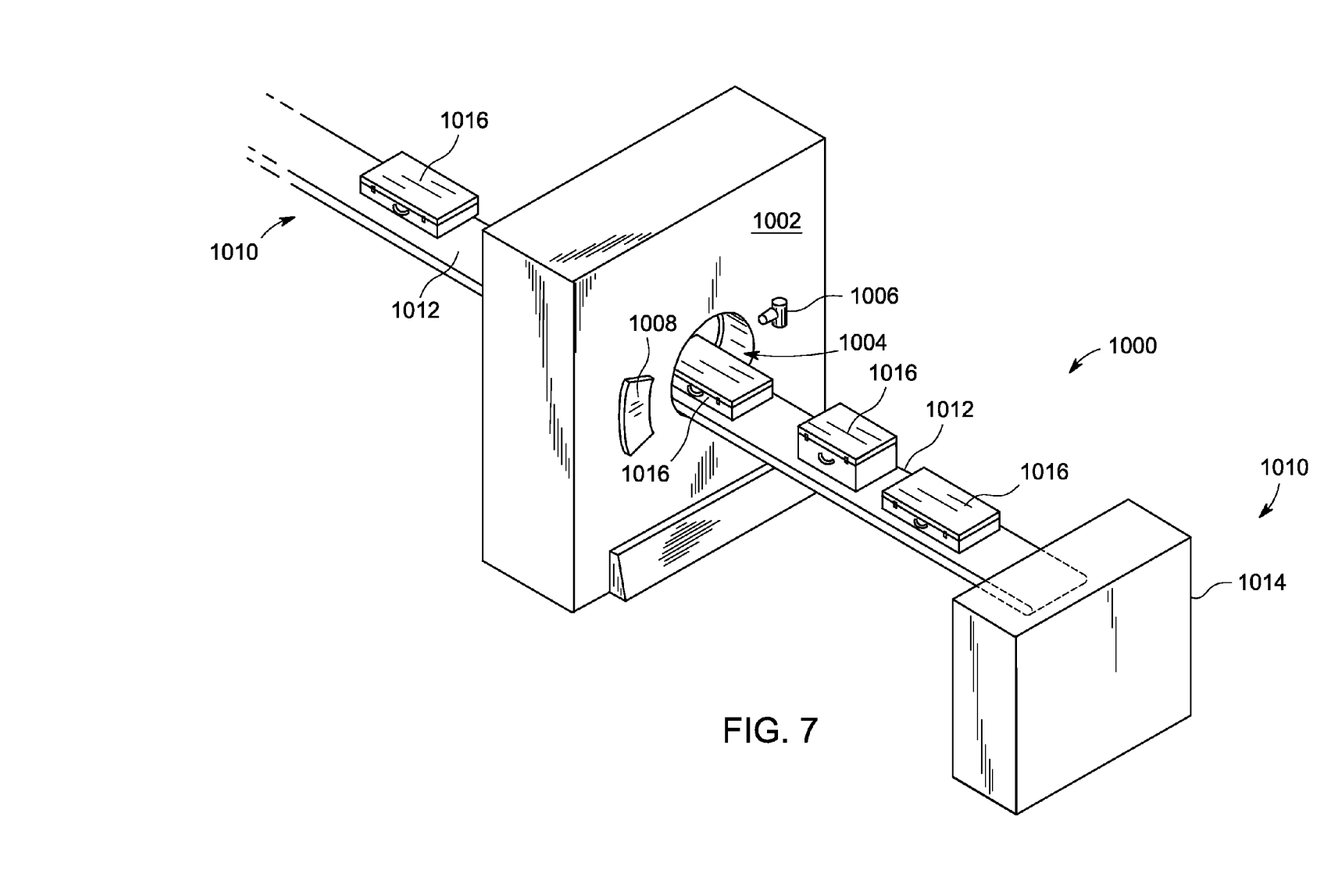
FIG. 7 is a pictorial view of a baggage scanning system incorporating embodiments of the invention.

Referring now to FIG. 7, there is shown a package/baggage inspection system 1000 that can use the data acquisition technique according to embodiments of the invention and which includes a rotatable gantry 1002 having an opening 1004 therein through which packages or pieces of baggage may pass. The rotatable gantry 1002 houses one or more x-ray energy sources 1006 as well as a detector assembly 1008 having scintillator arrays comprised of scintillator cells. A conveyor system 1010 is also provided and includes a conveyor belt 1012 supported by structure 1014 to automatically and continuously pass packages or baggage pieces 1016 through opening 1004 to be scanned. Objects 1016 are passed through opening 1004 by conveyor belt 1012, imaging data is then acquired, and the conveyor belt 1012 removes the packages 1016 from opening 1004 in a controlled and continuous manner. As a result, postal inspectors, baggage handlers, and other security personnel may non-invasively inspect the contents of packages 1016 for explosives, knives, guns, contraband, etc.

An implementation of embodiments of the invention in an example comprises a plurality of components such as one or more of electronic components, hardware components, and/or computer software components. A number of such components can be combined or divided in an implementation of the embodiments of the invention. An exemplary component of an implementation of the embodiments of the invention employs and/or comprises a set and/or series of computer instructions written in or implemented with any of a number of programming languages, as will be appreciated by those skilled in the art.

An implementation of the embodiments of the invention in an example employs one or more computer readable storage media. An example of a computer-readable signal-bearing medium for an implementation of the embodiments of the invention comprises the recordable data storage medium of the image reconstructor 34, and/or the mass storage device 38 of the computer 36. A computer-readable storage medium for an implementation of the embodiments of the invention in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory.

According to one embodiment of the invention, a tomographic system includes a gantry having an opening for receiving an object to be scanned, a radiation source, a detector positioned to receive radiation from the source that passes through the object, and a computer programmed to acquire a plurality of helical projection datasets of the object, reconstruct a first image using the acquired plurality of helical projection datasets and using a first reconstruction algorithm, reconstruct a second image using the acquired plurality of helical projection datasets and using a second reconstruction algorithm that is different from the first reconstruction algorithm, extract frequency components from each of the first and second images, sum the frequency components from each of the first and second images, and inverse transform the sum of the frequency components to generate a final image.

According to another embodiment of the invention, a method of generating an image includes reconstructing first and second images from a set of helical projection datasets using reconstruction algorithms that are different from one another, extracting frequency information from each of the first and second images, summing the extracted frequency data from each of the first and second images, and transforming the summed frequency data using an inverse transform to generate an image.

According to yet another embodiment of the invention, a computer readable storage medium having stored thereon a computer program comprising instructions, which, when executed by a computer, cause the computer to obtain helical projection datasets of a subject, reconstruct a first image of the subject using the helical projection datasets and a first reconstruction algorithm and a second image of the subject using the helical projection datasets and a second reconstruction algorithm that is different from the first reconstruction algorithm, extract frequency components from each of the first and second images, blend the extracted frequency components from each of the first and second images to form a blended dataset, and apply an inverse transform to the blended dataset to form an image.

A technical contribution for the disclosed method and apparatus is that it provides for a computer-implemented apparatus and method of reconstructing wide cone helical images using extracted frequency data from intermediate images formed using different reconstruction techniques.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A tomographic system comprising:
   a gantry having an opening for receiving an object to be scanned;
   a radiation source;
   a detector positioned to receive radiation from the source that passes through the object; and
   a computer programmed to:
      acquire a plurality of helical projection datasets of the object;

reconstruct a first image using the acquired plurality of helical projection datasets and using a first reconstruction algorithm;
reconstruct a second image using the acquired plurality of helical projection datasets and using a second reconstruction algorithm that is different from the first reconstruction algorithm;
extract frequency components from each of the first and second images;
sum the frequency components from each of the first and second images; and
inverse transform the sum of the frequency components to generate a final image.

2. The tomographic system of claim 1 wherein the computer is programmed to reconstruct the first image and the second image using the same plurality of helical projection datasets.

3. The tomographic system of claim 1 wherein the computer is programmed to reconstruct the first image using one of a FDK-type algorithm having a first weighting, an exact-type algorithm, and an iterative reconstruction.

4. The tomographic system of claim 3 wherein the computer is programmed to reconstruct the second image using one of the FDK-type algorithm having a second weighting that is different from the first weighting, the exact-type algorithm, and the iterative reconstruction.

5. The tomographic system of claim 4 wherein the exact-type algorithm is one of a Katsevich algorithm and a Pi-line algorithm.

6. The tomographic system of claim 1 wherein the computer is programmed to extract the frequency components from each of the first and second images by being programmed to:
transform the first image into a frequency domain using a transforming algorithm to generate first image frequency data;
transform the second image into the frequency domain using the transforming algorithm to generate second image frequency data;
apply a first mask to the first image frequency data; and
apply a second mask to the second image frequency data, wherein the second mask is a complementary mask of the first mask;
wherein when the computer is programmed to inverse transform the sum of the frequency components the computer is programmed to inverse transform the sum using an inverse of the same transforming algorithm used to generate the first image frequency data and the second image frequency data.

7. The tomographic system of claim 6 wherein the transforming algorithm is one of a Fast Fourier Transform (FFT), a wavelet transform, a discrete cosine transform, and a curvelet transform.

8. A method of generating an image comprising:
reconstructing first and second images from a set of helical projection datasets using reconstruction algorithms that are different from one another;
extracting frequency information from each of the first and second images;
summing the extracted frequency data from each of the first and second images; and
transforming the summed frequency data using an inverse transform to generate an image.

9. The method of claim 8 wherein reconstructing the first and second images comprises using the same set of helical projection datasets.

10. The method of claim 8 wherein reconstructing the first image comprises using one of a FDK-type algorithm having a first weighting, an exact-type algorithm, and an iterative reconstruction.

11. The method of claim 10 wherein reconstructing the second image comprises using one of the FDK-type algorithm having a second weighting, the exact-type algorithm, and the iterative reconstruction.

12. The method of claim 10 wherein the exact-type algorithm is one of a Katsevich algorithm and a Pi-line algorithm.

13. The method of claim 8 wherein extracting the frequency information from each of the first and second images comprises:
transforming the first image into a frequency domain using a transforming algorithm to generate first image frequency data;
transforming the second image into the frequency domain using the transforming algorithm to generate second image frequency data;
applying a first mask to the first image frequency data; and
applying a second mask to the second image frequency data, wherein the second mask is a complementary mask of the first mask;
wherein transforming the summed frequency data using the inverse transform comprises inverse transforming the sum using an inverse of the same transforming algorithm used to generate the first image frequency data and the second image frequency data.

14. The method of claim 13 wherein the transforming algorithm is one of a Fast Fourier Transform (FFT), a wavelet transform, a discrete cosine transform, and a curvelet transform.

15. A non-transitory computer readable storage medium having stored thereon a computer program comprising instructions, which, when executed by a computer, cause the computer to:
obtain helical projection datasets of a subject;
reconstruct:
a first image of the subject using the helical projection datasets and a first reconstruction algorithm; and
a second image of the subject using the helical projection datasets and a second reconstruction algorithm that is different from the first reconstruction algorithm;
extract frequency components from each of the first and second images;
blend the extracted frequency components from each of the first and second images to form a blended dataset; and
apply an inverse transform to the blended dataset to form an image.

16. The non-transitory computer readable storage medium of claim 15 wherein the computer is further caused to reconstruct the first image and the second image using the same helical projection datasets.

17. The non-transitory computer readable storage medium of claim 15 wherein the computer is further caused to reconstruct the first and second images using one of a FDK-type algorithm having a first weighting, the FDK-type algorithm having a second weighting, an exact-type algorithm, and an iterative reconstruction.

18. The non-transitory computer readable storage medium of claim 17 wherein the exact-type algorithm is one of a Katsevich algorithm and a Pi-line algorithm.

19. The non-transitory computer readable storage medium of claim 15 wherein the computer is further caused to extract the frequency components from each of the first and second images by being programmed to:

transform the first image into a frequency domain using a transforming algorithm to generate first image frequency data;

transform the second image into the frequency domain using the transforming algorithm to generate second image frequency data;

apply a first mask to the first image frequency data; and apply a second mask to the second image frequency data, wherein the second mask is a complementary mask of the first mask;

wherein when the computer is caused to apply the inverse transform to the blended dataset the computer is caused to inverse transform the blended dataset using an inverse of the same transforming algorithm used to generate the first image frequency data and the second image frequency data.

20. The non-transitory computer readable storage medium of claim 19 wherein the transforming algorithm is one of a Fast Fourier Transform (FFT), a wavelet transform, a discrete cosine transform, and a curvelet transform.

* * * * *